(12) United States Patent
Hefner, Jr.

(10) Patent No.: US 8,962,792 B2
(45) Date of Patent: Feb. 24, 2015

(54) PROCESS FOR PREPARING EPOXY RESINS

(75) Inventor: Robert E. Hefner, Jr., Rosharon, TX (US)

(73) Assignee: Dow Global Technologies LLC, Midland, MI (US)

( * ) Notice: Subject to any disclaimer, the term of this patent is extended or adjusted under 35 U.S.C. 154(b) by 46 days.

(21) Appl. No.: 13/816,258

(22) PCT Filed: Sep. 7, 2011

(86) PCT No.: PCT/US2011/050597
§ 371 (c)(1),
(2), (4) Date: Feb. 11, 2013

(87) PCT Pub. No.: WO2012/044442
PCT Pub. Date: Apr. 5, 2012

(65) Prior Publication Data
US 2013/0178601 A1    Jul. 11, 2013

Related U.S. Application Data

(60) Provisional application No. 61/388,085, filed on Sep. 30, 2010.

(51) Int. Cl.
C08G 59/02    (2006.01)
C08G 59/14    (2006.01)
(Continued)

(52) U.S. Cl.
CPC .......... C08G 65/2696 (2013.01); C07D 301/28 (2013.01);
(Continued)

(58) Field of Classification Search
CPC ........................................................ C08G 59/02
USPC .......... 528/408, 403, 482, 488, 489, 501, 503
See application file for complete search history.

(56) References Cited

U.S. PATENT DOCUMENTS 3,256,226 A    6/1966   Fekete et al.
(Continued)

FOREIGN PATENT DOCUMENTS

EP               012160 A1    6/1980
(Continued)

OTHER PUBLICATIONS

Taira, Kazunari, et al., Journal of the American Chemical Society, Jun. 8, 1984, 7831-7835, V. 106.
(Continued)

*Primary Examiner* — Duc Truong (57) ABSTRACT

A process for preparing an aliphatic or cycloaliphatic epoxy resin including the steps of: (I) reacting a mixture of (a) an aliphatic or cycloaliphatic hydroxyl containing material, (b) an epihalohydrin, (c) a basic acting substance, (d) a non-Lewis acid catalyst, and (e) optionally, a solvent, forming an epoxy resin composition; (II) subjecting the epoxy resin composition produced in step (I) to a separation process to remove (A) "light" components such as, for example, solvent used in the epoxidation reaction, if any, unreacted epihalohydrin, and co-products such as di(epoxypropyl)ether; (B) unreacted aliphatic or cycloaliphatic hydroxyl containing material, if any; (C) partially epoxidized aliphatic or cycloaliphatic hydroxyl containing material, such as, for example, MGE; (D) fully epoxidized aliphatic or cycloaliphatic hydroxyl containing material, such as, for example, DGE, such that the (E) aliphatic or cycloaliphatic polyfunctional epoxy resin product remaining contains no more than 50% by weight of said fully epoxidized aliphatic or cycloaliphatic hydroxyl containing material (D); and (III) recycling the isolated partially epoxidized aliphatic or cycloaliphatic hydroxyl containing material (C) and any mixtures of partially epoxidized aliphatic or cycloaliphatic hydroxyl containing material (C) with fully epoxidized aliphatic or cycloaliphatic hydroxyl containing material (D) from step (II) to a new reaction mixture of step (I).

17 Claims, 2 Drawing Sheets

(51) Int. Cl.
*C08G 65/26* (2006.01)
*C07D 301/28* (2006.01)
*C07D 301/32* (2006.01)
*C08G 65/04* (2006.01)
*C08G 59/00* (2006.01)

(52) U.S. Cl.
CPC ............ *C07D 301/32* (2013.01); *C08G 59/025* (2013.01)
USPC ........... 528/408; 528/403; 528/482; 528/488; 528/489; 528/501; 528/503

(56) References Cited

U.S. PATENT DOCUMENTS

| | | |
|---|---|---|
| 3,271,363 A | 9/1966 | Nikles et al. |
| 3,639,655 A | 2/1972 | Jones |
| 3,864,316 A | 2/1975 | Robinson |
| 4,125,558 A | 11/1978 | Torsi |
| 4,284,574 A | 8/1981 | Bagga |
| 4,373,073 A | 2/1983 | Wojtech et al. |
| 4,417,033 A | 11/1983 | Bowditch |
| 4,544,731 A | 10/1985 | Cavitt et al. |
| 5,128,491 A | 7/1992 | Cheng |
| 5,780,582 A | 7/1998 | Wang et al. |
| 5,959,061 A | 9/1999 | Neumann et al. |
| 6,211,389 B1 | 4/2001 | Dimke |
| 6,410,807 B1 | 6/2002 | Yang et al. |
| 6,677,468 B1 | 1/2004 | Dimke et al. |
| 8,318,834 B2 | 11/2012 | Hefner, Jr. et al. |
| 2002/0161106 A1 | 10/2002 | Anderson |
| 2006/0235183 A1 | 10/2006 | Ogura et al. |
| 2007/0087146 A1 | 4/2007 | Evans et al. |
| 2007/0117938 A1 | 5/2007 | Martz et al. |
| 2007/0281179 A1 | 12/2007 | Ambrose et al. |
| 2011/0039982 A1 | 2/2011 | Hefner, Jr. et al. |
| 2011/0040046 A1 | 2/2011 | Hefner, Jr. et al. |
| 2011/0054056 A1 | 3/2011 | Hefner, Jr. et al. |

FOREIGN PATENT DOCUMENTS

| | | |
|---|---|---|
| EP | 0121260 A2 | 10/1984 |
| EP | 0253405 A2 | 1/1988 |
| EP | 0702042 A1 | 3/1996 |
| GB | 120476 A | 11/1918 |
| JP | 200700915 | 1/2007 |
| WO | 9510556 A1 | 4/1995 |
| WO | 0001779 A1 | 1/2000 |
| WO | 03078512 A1 | 9/2003 |
| WO | 2007/078859 A2 | 7/2007 |
| WO | 2008045882 A1 | 4/2008 |
| WO | 2008045884 A1 | 4/2008 |
| WO | 2008045889 A1 | 4/2008 |
| WO | 2008045894 A1 | 4/2008 |
| WO | 2009/105938 A1 | 9/2009 |
| WO | 2009142898 A1 | 11/2009 |
| WO | 2009142900 A1 | 11/2009 |
| WO | 2009142901 A1 | 11/2009 |
| WO | 2012/044443 A1 | 4/2012 |
| WO | 2012/044455 A1 | 4/2012 |
| WO | 2012/050777 A1 | 4/2012 |
| WO | 2012044458 A1 | 4/2012 |

OTHER PUBLICATIONS

PCT/US2011/050597, International Search Report.
PCT/US2011/050597, Written Opinion of the International Searching Authority.
PCT/US2011/050597, International Preliminary Report on Patentability.
PCT US2011050742, International Preliminary Report on Patentability.
PCTUS2011049840, International Preliminary Report on Patentability.
PCTUS2011049840, International Search Report.
PCTUS2011049840, Written Opinion of the International Searching Authority.
PCTUS2011050613, International Preliminary Report on Patentability.
PCTUS2011050613, International Search Report and Written Opinion.
PCTUS2011050742, International Search Report and Written Opinion of the International Searching Authority.
PCTUS2011051291, International Preliminary Report on Patentability.
PCTUS2011051291, International Search Report.
PCTUS2011051291, Written Opinion of the International Searching Authority.
PCTUS2011051482, International Preliminary Report on Patentability.
PCTUS2011051482, International Search Report and Written Opinion of the International Searching Authority.
PCTUS2011052236 International Preliminary Report on Patentability.
PCTUS2011052236 International Search Report and Written Opinion of the International Searching Authority.
PCTUS2011052672, International Preliminary Report on Patentability.
PCTUS2011052672, International Search Report.
PCTUS2011052672, Written Opinion of the International Searching Authority.
Dean, J.M., et al., Journal of Polymer Science, Part B: Polymer Physics, 2001, pp. 2996-3010, vol. 39.
U.S. Appl. No. 61/157,380, 2009.
U.S. Appl. No. 61/388,059, 2010.
White, S.R., et al, Nature, Autonomic Healing of Polymer Composites, 2001, pp. 409-794.

PROCESS FOR PREPARING EPOXY RESINS

This application is a non-provisional application claiming priority from the U.S. Provisional Patent Application No. 61/388,085, filed on Sep. 30, 2010, entitled "PROCESS FOR PREPARING EPDXY RESINS" the teachings of which are incorporated by reference herein, as if reproduced in full hereinbelow.

BACKGROUND OF THE INVENTION

1. Field of the Invention

The present invention is related to a process for preparing aliphatic or cycloaliphatic epoxy resins.

2. Description of Background and Related Art

Epoxidation of aliphatic and cycloaliphatic alcohols is an area of long standing interest, for example as described in EP 0 121 260. Disclosed in EP 0 121 260 are examples of phase transfer catalyzed epoxidation of aliphatic diols using quaternary ammonium halide catalysts with epichlorohydrin, including cyclohexanedimethanol (isomers unspecified).

Chemistry and processes for the manufacture of aliphatic and cycloaliphatic epoxy resins via epoxidation of aliphatic and cycloaliphatic hydroxyl containing materials using an epihalohydrin is difficult, if not impossible, to drive to full conversion and produces significant quantities of partially epoxidized products, such as, for example, monoglycidyl ether (MGE) (as much as 2-20 weight percent (wt %) of the epoxy resin composition), as well as oligomeric co-products (as much as 25-40 wt % of the epoxy resin composition). While various methods, such as, for example, distillation, are operable for removal of unconverted aliphatic and cycloaliphatic hydroxyl containing reactant, MGE, diglycidyl ether (DGE) product, and the like, no satisfactory solution exists for dealing with partially epoxidized products such as MGE, once removed.

Another complication is that while the recovered unconverted aliphatic and cycloaliphatic hydroxyl containing reactant may be reused as reactant in a new epoxidation, most methods used for recovery will only provide aliphatic and cycloaliphatic hydroxyl containing reactant containing a contaminating amount of MGE. Likewise, most methods used for removal and recovery of MGE will only produce a product containing both MGE and DGE.

The best solution to date has been use of the aliphatic and cycloaliphatic epoxy resins as reactive diluents for epoxy resins where the unreacted aliphatic and cycloaliphatic hydroxyl containing material, MGE, the desired DGE and the oligomeric co-products are simply carried into the total diluent and epoxy resin composition. Problems with this approach include (1) reduction of mechanical properties induced by any unreacted aliphatic and cycloaliphatic hydroxyl containing material or even leaching of said material from a thermoset product, (2) reduction of reactivity with curing agents and chain termination caused by monofunctionality of the MGE resulting in reduction of mechanical properties, and (3) higher than desirable viscosities induced by the presence of the oligomeric co-products and reduced reactivity with curing agents.

Thus, it would be highly desirable to be able to fractionate an aliphatic or cycloaliphatic epoxy resin to specifically provide DGE for use as a low viscosity and highly reactive epoxy resin diluent or reactant for epoxy resin advancement while simultaneously providing a viable end use for any MGE plus unreacted aliphatic and cycloaliphatic hydroxyl containing material, MGE, and MGE plus DGE fractions that result. It should be noted that the aforementioned discussion centers upon epoxidation processes where the aliphatic and cycloaliphatic hydroxyl containing material is a diol, however, the term "aliphatic and cycloaliphatic hydroxyl containing material" is intended to include higher functional materials such as triols.

WO/2009/142901, incorporated herein by reference, describes an epoxy resin composition prepared from a mixture of cis-, trans-1,3- and 1,4-cyclohexanedimethanols using a wide variety of epoxidation processes. Additionally demonstrated in the examples of WO/2009/142901 is the preparation of various distilled grades of the MGE and DGE of cis-, trans-1,3- and 1,4-cyclohexanedimethanols, including high purity (>99 wt %) DGE.

Typically, in preparing the high purity DGE product by the process of WO2009/142901, a residual amount of unreacted aliphatic or cycloaliphatic diol, MGE, DGE, and oligomeric products are formed during the reaction process disclosed in WO2009/142901. Thus, distillation methods are typically employed after the epoxidation process of WO2009/142901 in order to remove the unwanted unreacted aliphatic or cycloaliphatic diol, MGE, and any other higher boiling oligomeric materials from the desired the DGE product. The resulting high purity DGE can then be used in the aforementioned advancement chemistry or as a reactive epoxy resin diluent.

After the desired high purity DGE product is substantially removed using a distillation column as taught in the WO2009/142901 process, an undesired co-product produced from the distillation process usually includes (1) an unreacted aliphatic or cycloaliphatic diol stream containing minor amounts of MGE, (2) a MGE stream, and (3) a MGE and DGE stream. Generally, in order for a process for preparing purified DGE to be industrially practical and commercially viable, something useful must be done with the unwanted co-products such as the co-produced unwanted MGE containing fractions from the distillation process in order to recover the value from such co-products.

Extensive research is ongoing to develop can coating resins based on high purity DGE of cycloaliphatic hydroxyl containing materials such as UNOXOL™ Diol. [UNOXOL™ cyclic dialcohol is a registered trademark of Union Carbide Corporation.] The scale-up of the epoxidation of UNOXOL™ Diol normally yields significant quantities of the MGE and MGE/DGE fractions from the distillation operation to recover high purity DGE. It would be desirable to find a process for handling the resultant MGE and MGE/DGE fractions from distillation without detrimentally impacting the epoxidation reaction process to produce high purity DGE for the can coating applications.

Heretofore, a process for the specific recycle of the MGE containing fractions obtained, for example, from the distillation of an aliphatic or cycloaliphatic epoxy resin into an epoxidation to recover useful products from said MGE containing fractions has not been done before in an epoxidation process for aliphatic and cycloaliphatic hydroxyl containing materials.

It is therefore desired to provide a process for recovering the MGE containing fractions from the fractionation of an aliphatic or cycloaliphatic epoxy resin and recycling the MGE containing fractions into an epoxidation reaction process for converting the MGE into useful materials such as DGE or polyfunctional aliphatic or cycloaliphatic epoxy resin.

SUMMARY OF THE INVENTION

A "monoglycidyl ether-containing product or MGE-containing product" herein means a partially epoxidized aliphatic or cycloaliphatic hydroxyl containing material, such as, for example, monoglycidyl ether, per se, or a monoglycidyl ether-containing material, i.e., a product mixture containing as one component, a monoglycidyl ether such as for example a mixture of MGE and DGE. The MGE-containing product is a fraction which is co-produced during an epoxidation process for producing an aliphatic or cycloaliphatic epoxy resin product; wherein the co-produced MGE-containing product fraction and the aliphatic or cycloaliphatic epoxy resin product resultant mixture after the epoxidation process is subjected to a subsequent separation process such that the co-produced MGE-containing product fraction is substantially separated and isolated from the aliphatic or cycloaliphatic epoxy resin product. The separation process can be carried out by a known means such as, for example, a distillation unit operation. Once the co-produced MGE-containing product fraction is separated from the aliphatic or cycloaliphatic epoxy resin product, for example by distillation, the resulting separated/isolated MGE-containing product fraction, typically one or more cuts taken in a distillation process, comprises the MGE-containing product useful in the present invention.

This present invention provides a viable technology for handling the isolated MGE-containing product inherently produced in the process used to concomitantly recover high purity DGE and polyfunctional aliphatic or cycloaliphatic oligomeric epoxy resin product. Generally, the present invention provides a specific epoxidation and recycle process which can be employed to selectively convert MGE-containing product to an epoxy resin product such as (1) an aliphatic or cycloaliphatic epoxy resin product and/or (2) a polyfunctional aliphatic or cycloaliphatic epoxy (PACE) resin product.

In one broad embodiment, the present invention provides a process for recycling MGE and/or MGE containing material to an epoxidation reaction mixture and selectively converting at least a portion of the MGE and/or MGE containing material to a desired DGE product and/or to a desired PACE resin product.

In another embodiment, the present invention is directed to a process for preparing an aliphatic or cycloaliphatic epoxy resin including the steps of:

(I) reacting a mixture of (a) an aliphatic or cycloaliphatic hydroxyl containing material, (b) an epihalohydrin, (c) a basic acting substance, (d) a non-Lewis acid catalyst, and (e) optionally, a solvent, forming an epoxy resin composition;

(II) subjecting the epoxy resin composition produced in step (I) to a separation process to remove (A) "light" components such as, for example, solvent used in the epoxidation reaction, if any, unreacted epihalohydrin, and co-products such as di(epoxypropyl)ether; (B) unreacted aliphatic or cycloaliphatic hydroxyl containing material, if any; (C) partially epoxidized aliphatic or cycloaliphatic hydroxyl containing material, such as, for example, MGE; (D) fully epoxidized aliphatic or cycloaliphatic hydroxyl containing material, such as, for example, DGE, such that the (E) PACE resin product remaining contains no more than 50 wt % of said fully epoxidized aliphatic or cycloaliphatic hydroxyl containing material (D); and (III) recycling the isolated partially epoxidized aliphatic or cycloaliphatic hydroxyl containing material (C) and any mixtures of partially epoxidized aliphatic or cycloaliphatic hydroxyl containing material (C) with fully epoxidized aliphatic or cycloaliphatic hydroxyl containing material (D) from step (II) to a reaction mixture of step (I).

In one embodiment of the present invention, recycle of MGE or MGE and DGE fractions isolated from the epoxy resin of an aliphatic or cycloaliphatic epoxy resin is performed into an epoxidation specifically at the initial stage of aqueous alkaline agent (NaOH, for example) addition in an epoxidation process using 2 or more stages of aqueous alkaline agent addition. Unexpectedly, increased yields of PACE resin are obtained concurrent with reduced yields of MGE while maintaining DGE yield (overall yield of combined MGE and DGE is reduced) (compare Example 1 and Comparative Example A, herein).

In another embodiment of the present invention, recycle of MGE or MGE and DGE fractions isolated from the epoxy resin of an aliphatic or cycloaliphatic epoxy resin is performed into an epoxidation specifically at the final stage of aqueous alkaline agent (NaOH, for example) addition in an epoxidation process using 2 or more stages of aqueous alkaline agent addition. Unexpectedly, increased yields of DGE are obtained while decreasing the yield of undesirable MGE (overall yield of combined MGE and DGE is maintained) while the yield of PACE resin is decreased (compare Example 2 and Comparative Example B, herein).

The recycle process of the present invention may be broadly applied to the production of aliphatic and cycloaliphatic epoxy resins, especially and preferably those produced via non-Lewis acid catalyzed epoxidations. The process of the present invention advantageously minimizes the yield of undesirable MGE while (1) maximizing the yield of DGE without increasing the yield of the PACE resin or while (2) maintaining the yield of DGE and increasing the yield of the PACE resin. Furthermore, the recycle process of the present invention exhibits unexpectedly high selectivity, with no additional structures being detected as a result of the recycle of MGE or MGE and DGE.

Can coating compositions are described in co-pending U.S. Patent Application Ser. No. 61/388,077, entitled "COATING COMPOSITIONS", filed of even date herewith by Xin Jin et al.; and an advanced epoxy resin product is described in co-pending U.S. Patent Application Ser. No. 61/388,071, entitled "ADVANCED EPDXY RESIN COMPOSITIONS", filed of even date herewith by Xin Jin et al.; both incorporated herein by reference. The technology disclosed in the above U.S. patent applications depends on the production of a high purity (>98%) cycloaliphatic DGE, such as, for example, the DGE of UNOXOL™ Diol.

PACE resin (A) and the processes for preparing the same is provided in co-pending U.S. Patent Application Ser. No. 61/388,059 entitled "THERMOSETTABLE COMPOSITIONS AND THERMOSETS THEREFROM", filed of even date herewith by Robert Hefner, Jr.; and in co-pending U.S. Patent Application Ser. No. 61/388,064 entitled "EPDXY RESIN COMPOSITIONS", filed of even date herewith by Robert Hefner, Jr., both incorporated herein by reference. The technology disclosed in the above U.S. patent applications, which is highly useful for the preparation of coatings with excellent solvent resistant, moisture resistant, abrasion resistant, impact resistant, and weatherable (UV resistant, non-chalking) properties, depends on isolation of the PACE resin from the epoxy resin of an aliphatic or cycloaliphatic hydroxyl containing material.

Epoxidation of aliphatic and cycloaliphatic hydroxyl containing materials using an epihalohydrin and non-Lewis acid catalysis is difficult, if not impossible, to drive to full conversion even under conditions of increased reaction time and/or temperature, normally employed in an attempt to increase conversion of aliphatic and cycloaliphatic hydroxyl containing materials or intermediates thereof, such as, for example, MGE to the desired DGE. Thus, the epoxy resin of an aliphatic or cycloaliphatic diol will typically contain minor amounts of (1) unconverted aliphatic or cycloaliphatic diol, (2) aliphatic or cycloaliphatic MGE, (3) aliphatic or cycloaliphatic DGE and (4) oligomeric co-products (PACE resin). Resolution of the various constituents of this epoxy resin, for example, via vacuum distillation, results in distillation cuts which contain MGE or MGE and DGE. Without the method of the present invention for recycle of these MGE rich fractions or a separate end-use for said fractions, significant loss in yield and value of product may result. The present invention provides an epoxidation and recycle process having broad utility for epoxidation of aliphatic and/or cycloaliphatic hydroxyl containing reactants.

BRIEF DESCRIPTION OF THE DRAWINGS

For the purpose of illustrating the present invention, the drawings show a form of the present invention which is presently preferred. However, it should be understood that the present invention is not limited to the embodiments shown in the drawings.

DETAILED DESCRIPTION OF THE INVENTION

One broad embodiment of the present invention comprises a process for preparing an epoxy resin such as (1) an aliphatic or cycloaliphatic epoxy resin product and/or (2) a PACE resin product including the process steps of (I) epoxidation, (II) fractionation, and (III) recycling.

As aforementioned, the term "monoglycidyl ether-containing product or MGE-containing product" herein means a monoglycidyl ether, per se, or a monoglycidyl ether-containing material, i.e., a product mixture containing as one component, a MGE such as for example a mixture of MGE and DGE. The term "MGE-containing product", also referred to herein interchangeably as a "co-product" or a "second product", is used herein to mean a MGE-containing product isolated and separated from a first epoxy resin product; wherein the first epoxy resin product and second MGE-containing product or co-product are formed as a result of an epoxidation reaction of (i) an aliphatic or cycloaliphatic hydroxyl containing material, using (ii) an epihalohydrin, and (iii) a basic-acting substance, in the presence of (iv) a non-Lewis acid catalyst; and optionally, (v) one or more solvents.

The isolated MGE-containing product comprises the product after removal of (1) "light" components, such as, for example, solvents used in the epoxidation reaction, if any, unreacted epihalohydrin, and co-products such as di(epoxypropyl)ether; (2) unreacted aliphatic or cycloaliphatic hydroxyl containing material, if any; (3) fully epoxidized aliphatic or cycloaliphatic hydroxyl containing material, such as, for example, DGE; and (4) PACE resin product remaining as the bottoms of the separation process.

The MGE-containing product useful in the present invention is produced as a second product stream during the production of a first epoxy resin product stream by epoxidizing an aliphatic or cycloaliphatic hydroxyl containing material, particularly an aliphatic or cycloaliphatic diol such as described in aforementioned WO2009/142901. After the epoxidation reaction, the MGE-containing product (second resin product stream) is separated and isolated from the first epoxy resin product stream.

Figure 1:
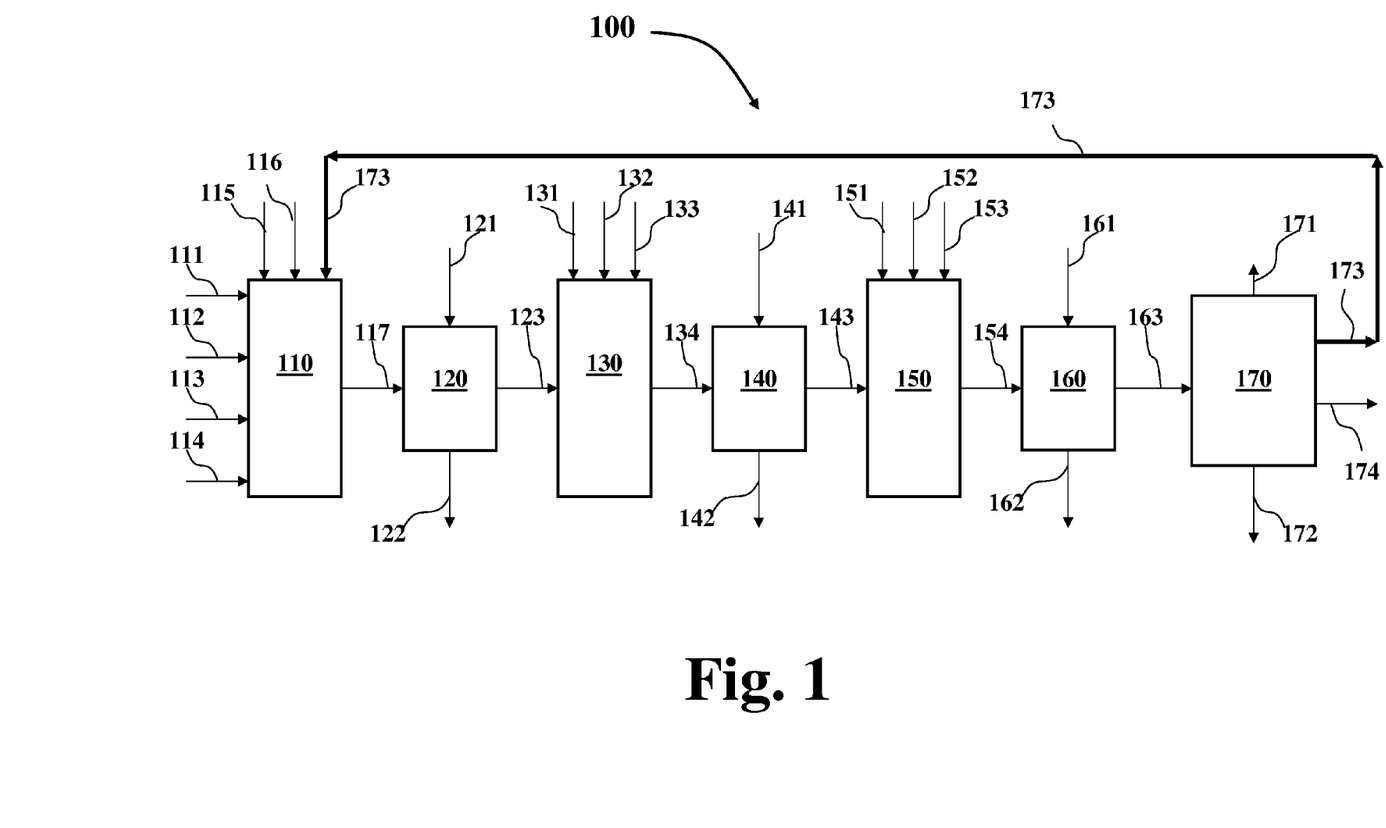
FIG. 1 is a schematic flow diagram showing one embodiment of a recycle process of the present invention in the production of an epoxy resin product.

With reference to FIG. 1, there is shown a general process for manufacturing an epoxy resin composition of the present invention, the process generally indicated by reference numeral 100. FIG. 1 shows a series of epoxidation stages, 110, 130, and 150 followed by a washing step after each stage including 120, 140 and 160, respectively. It should be understood that the number of epoxidation stages and washing steps used in present invention process may comprise one, two or more stages and the present invention is not limited to the embodiment shown in FIG. 1 which shows three epoxidation stages and three wash steps. In other embodiments, two or more stages or steps of the present invention may be combined and carried out by one apparatus or by two or more separate apparatuses.

With reference to FIG. 1 again, the process 100 includes an aliphatic or cycloaliphatic hydroxyl containing material feed stream 111, an epihalohydrin feed stream 112, a non-Lewis acid catalyst feed stream 113, and a solvent stream 114 along with a basic-acting substance feed stream 115 and an inert gas such as a nitrogen stream 116 are fed into the first epoxidation reaction stage 110 to carry out a first epoxidation reaction. A recycle feed stream 173 (described below) is also forwarded to the first epoxidation reaction stage 110. After the first epoxidation reaction, a resultant first epoxidation product, stream 117 from the first stage 110, is washed with a water stream 121 at the first washing stage 120 as an aqueous waste stream 122 is directed to a waste recovery operation (not shown) or to another operation for further processing. A washed epoxidation product stream 123 exits from the first washing stage 120.

The washed epoxidation product stream 123 from the first washing stage 120 is forwarded to a second epoxidation stage 130 wherein a second non-Lewis acid catalyst feed stream 131, a second basic-acting substance feed stream 131 and a second inert gas such as a nitrogen stream 132 are fed into the second epoxidation reaction stage 130 to carry out further epoxidation of the washed epoxidation product stream 123 from the first washing stage 120 to form a second epoxidation product stream 134. In an optional embodiment, a second epihalohydrin stream (not shown) and a second solvent stream (not shown) made be fed into the second epoxidation stage 130 if desired. After the second epoxidation reaction, the resultant second epoxidation product, stream 134 from the second stage 130, is washed with a water stream 141 at the second washing stage 140 as an aqueous waste stream 142 is directed to a waste recovery operation (not shown) or to another operation for further processing. A washed epoxidation product stream 143 exits from the second washing stage 140.

The washed epoxidation product stream 143 from the second washing stage 140 is forwarded to a third epoxidation stage 150 wherein a third non-Lewis acid catalyst feed stream 151, a third basic-acting substance feed stream 152 and a third inert gas such as a nitrogen stream 153 are fed into the third epoxidation reaction stage 150 to carry out further epoxidation of the washed epoxidation product stream 143 from the second washing stage 140 to form a third epoxidation product stream 154. In an optional embodiment, a third epihalohydrin stream (not shown) and a third solvent stream (not shown) made be fed into the third epoxidation stage 150 if desired. After the third epoxidation reaction, the resultant third epoxidation product, stream 154 from the third stage 150, is washed with a water stream 161 at the third washing stage 160 as an aqueous waste stream 162 is directed to a waste recovery operation (not shown) or to another operation for further processing. A washed epoxidation product stream 163 exits from the third washing stage 160.

Optionally, in one embodiment, the washed epoxidation product stream 163 from the third washing stage 160 may be forwarded to a devolatilization operation (not shown) to remove any lights (not shown) from the washed epoxidation product 163 to form a crude epoxidation product stream (not shown). In the embodiment shown in FIG. 1, the washed epoxidation product stream 163 is forwarded to a fractionation operation 170 wherein a top lights stream 171, a bottoms stream 172, a partially or partially/fully epoxidized aliphatic or cycloaliphatic hydroxyl containing material stream 173, and a fully epoxidized aliphatic or cycloaliphatic hydroxyl containing material stream 174 are produced. The fully epoxidized aliphatic or cycloaliphatic hydroxyl containing material stream 174 is a purified epoxy resin product which can be used in subsequent processes. The bottoms stream 172 of this embodiment is an example of a polyfunctional aliphatic or cycloaliphatic epoxy (PACE) resin which can also be used in subsequent processes. In the embodiment shown in FIG. 1, the partially or partially/fully epoxidized aliphatic or cycloaliphatic hydroxyl containing material stream 173 is recycled from the fractionation operation 170 to the first epoxidation reaction stage 110.

Figure 2:
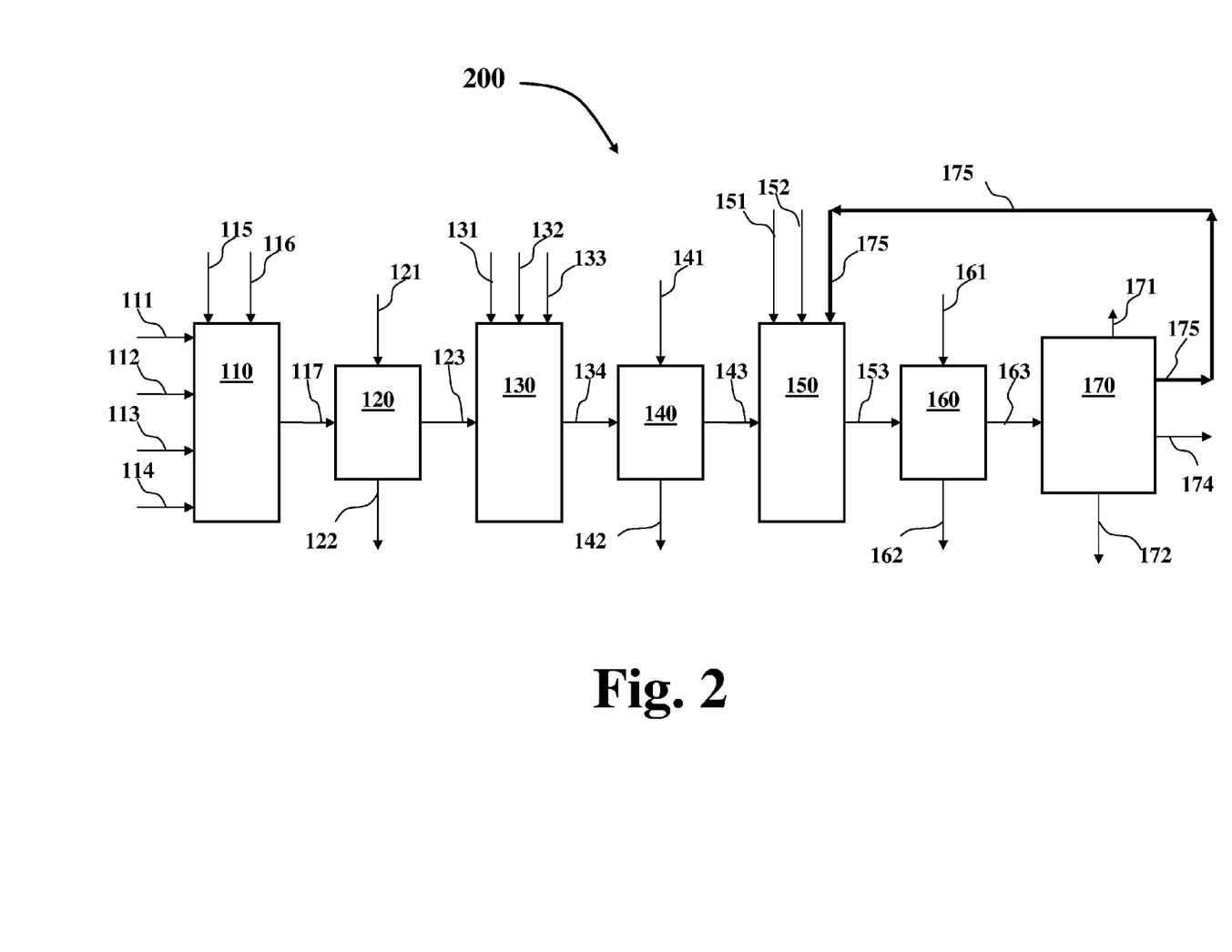
FIG. 2 is a schematic flow diagram showing another embodiment of a recycle process of the present invention in the production of an epoxy resin product.

With reference to FIG. 2, there is shown another general process for manufacturing an epoxy resin composition of the present invention, the process generally indicated by reference numeral 200. In the embodiment shown in FIG. 2, the process is similar to the process shown in FIG. 1 and like reference numerals are used in FIG. 2 as the reference numerals in FIG. 1 to show the same stages, steps or operations.

One different embodiment between the process shown in FIG. 1 and the process shown in FIG. 2 includes recycling a partially or partially/fully epoxidized aliphatic or cycloaliphatic hydroxyl containing material stream 175 of FIG. 2 from the fractionation operation 170 to the third epoxidation reaction stage 150. Although not shown, it should be understood that the recycle streams 173 or 175 may be recycled to any one, two or more, or all of the stages, steps or operations shown in FIG. 1 and FIG. 2.

It should be understood that any conventional equipment known to those skilled artisans can be used to carry out the manufacturing process of the present invention. For example, the equipment can include epoxidation reactor vessels; evaporation vessels such as rotary evaporators; and separation vessels such as distillation apparatus; which are known in the art. For example, generally, a separation vessel, such as a fractional vacuum distillation apparatus 170 may be used to produce several fractionation cuts including a "lights" stream 171, a "bottoms" stream 172 comprising unrecovered fully epoxidized aliphatic or cycloaliphatic hydroxyl containing material and oligomers, and a stream of partially or partially/fully epoxidized aliphatic or cycloaliphatic hydroxyl containing mixtures 173 or 175; and a high purity fully epoxidized aliphatic or cycloaliphatic hydroxyl containing material product stream 174. The bottoms stream 172 is separated and isolated from the other streams leaving the distillation apparatus. The high purity fully epoxidized aliphatic or cycloaliphatic hydroxyl containing material product stream shown in FIGS. 1 and 2 as stream 174 may be forwarded to a subsequent process to form curable compositions and thermosets therefrom; and the bottoms stream 172 may also be forwarded to a subsequent process to form curable compositions and thermosets therefrom. For example, these epoxy resin products can be mixed with a curing agent and/or a curing catalyst for making a thermosettable resin; and the thermosettable resin can be partially cured to form a B-stage material or completely cured to form a thermoset article.

The recycle process of the present invention includes as a first step an epoxidation step including reacting a mixture of (i) an aliphatic or cycloaliphatic hydroxyl containing material, (ii) an epihalohydrin, (iii) a basic acting substance, (iv) a non-Lewis acid catalyst, and (v) optionally, a solvent, forming an epoxy resin composition. The epoxidation step (I) of the present invention may be illustrated for example by the epoxidation of UNOXOL™ Diol according to the following generalized reaction scheme (geometric isomers not shown):

A specific example of the PACE resin is the aliphatic/cycloaliphatic polyfunctional epoxy resin isolated from the epoxy resin of cis-, trans-1,3- and 1,4-cyclohexanedimethanol. It is to be understood that the PACE resin comprises multiple components. For the PACE resin isolated from the epoxy resin of cis-, trans-1,3- and 1,4-cyclohexanedimethanol, the following components have been identified and may or may not be present in the individual products depending on the chemistry and processing employed to produce said epoxy resin (geometrical isomers and substitution are not shown in the chemical structures, the multiple geometrical isomers that are present are not given by the chemical names, other unidentified components may be present):

2-propanol, 1-(oxiranylmethoxy)-3-[[3(or 4)-[(oxiranyl-methoxy)methyl]cyclohexyl]methoxy]- oxirane, 2-[[[3(or 4)-[[2,3-bis(oxiranylmethoxy)propoxy]methyl]cyclohexyl]methoxy]methyl]- oxirane, 2-[[2-chloro-1-[[[3(or 4)-[(oxiranylmethoxy)methyl]cyclohexyl]methoxy]methyl]ethoxy]methyl]- cyclohexanemethanol, 3(or 4)-[[2-hydroxy-3-[[3(or 4)-[(oxiranylmethoxy)methyl]cyclohexyl]methoxy]propoxy]methyl]-

2-propanol, 1,3-bis[[3(or 4)-[(oxiranylmethoxy)methyl]cyclohexyl]methoxy]- oxirane, 2-[[2-[[3(or 4)-[(oxiranylmethoxy)methyl]-cyclohexyl]methoxy]-1-[[[3(or 4)-[(oxiranylmethoxy)methyl]cyclohexyl]methoxy]methyl]ethoxy]methyl]-

A minor amount of 3 isomeric monochloro compounds coelute with this latter triglycidyl ether.

Re-epoxidation of the PACE resin is used to beneficially modify the distribution of the components comprising said epoxy resin. Thus in the present specific example of the new compositions from the re-epoxidation of the PACE resin, the re-epoxidation process converts the diglycidyl ethers with a secondary hydroxyl group in their backbone to the corresponding triglycidyl ethers:

Epoxidation of aliphatic or cycloaliphatic hydroxyl containing materials is preferably performed in stages. A single stage comprises the addition of aqueous basic acting substance to the other reactants, catalyst and optional solvent, followed by post reaction and separation of the resultant spent aqueous phase, including precipitated salts, if any. When the epoxidation is performed in stages, such as, for example, in the non-Lewis acid catalyzed epoxidation process used in the examples of the present invention, the number of stages required will vary as a function of the specific reaction conditions used, the stoichiometry employed, the structure of the reactants and catalyst employed, and other known variables.

While the goal of the re-epoxidation process for most intended applications would be to fully convert the monohydroxy functional diglycidyl ethers to the corresponding triglycidyl ethers, respectively, via selective epoxidation of the secondary hydroxyl groups in the respective backbones, it is also operable to only partially convert these monohydroxy functional diglycidyl ethers to the corresponding triglycidyl ethers.

Specific epoxidation processes which may be employed in the present invention are delineated in WO 2009/142901 as well as in co-pending U.S. Patent Application Ser. No. 61/388,059 entitled "THERMOSETTABLE COMPOSITIONS AND THERMOSETS THEREFROM", filed of even date herewith by Robert Hefner, Jr.; and in co-pending U.S. Patent Application Ser. No. 61/388,064 entitled "EPOXY RESIN COMPOSITIONS", filed of even date herewith by Robert Hefner, Jr. As is disclosed therein, the epoxidation may optionally be run partially or totally under vacuum in a manner that removes all or a part of the water, for example via azeotropic distillation. Said epoxidation process typically comprises the steps of (1) coupling of the epihalohydrin with the aliphatic or cycloaliphatic hydroxyl-containing material and (2) dehydrohalogenation of the intermediate halohydrin thus formed. The process may be, for example, a phase transfer catalyzed epoxidation process, a slurry epoxidation process, or an anhydrous epoxidation process.

The epoxidation process may be carried out under various process conditions. For example, the temperature used in the epoxidation process is generally from about 20° C. to about 120° C., preferably from about 25° C. to about 60° C., and more preferably from about 30° C. to about 50° C. The pressure used in the epoxidation process is generally from about 0 mm Hg vacuum to about 100 psi, preferably from about 30 mm Hg vacuum to about 50 psi, and more preferably from about 60 mm Hg vacuum to about atmospheric pressure (e.g. 760 mm Hg). The time for completion of the epoxidation process is generally from about 1 hour to about 120 hours, more preferably from about 8 hours to about 72 hours, and most preferably from about 12 hours to about 48 hours.

For example, the use of 33% aqueous sodium hydroxide versus 50% aqueous sodium hydroxide under otherwise comparable reaction conditions slows the rate of conversion of the aliphatic or cycloaliphatic hydroxyl containing material to epoxy resin. Typically, a minimum of 2 stages are employed in the non-Lewis acid catalyzed epoxidation process with a practical maximum of no more than 6 stages being employed, and preferably a maximum of 3 to 4 stages.

Any aliphatic or cycloaliphatic hydroxyl-containing reactant may be employed in the epoxidation to produce the epoxy resin from which the MGE and/or MGE/DGE is recovered for recycle into another epoxidation using any aliphatic or cycloaliphatic hydroxyl-containing reactant. Aliphatic or cycloaliphatic hydroxyl-containing materials which may be employed in the epoxidation process of the present invention may include for example any one or more of the following: (a) cyclohexanedialkanols and cyclohexenedialkanols such as UNOXOL™ Diol (cis-, trans-1,3- and 1,4-cyclohexanedimethanol) as a preferred cyclohexanedialkanol; (b) cyclohexanolmonoalkanols and cyclohexenolmonoalkanols, such as trans-2-(hydroxymethyl)cyclohexanol or 1-phenyl-cis-2-hydroxymethyl-r-1-cyclohexanol; (c) decahydronaphthalenedialkanols, octahydronaphthalenedialkanols and 1,2,3,4-tetrahydronaphthalenedialkanols, such as 1,2-decahydronaphthalenedimethanol; (d) bicyclohexanedialkanols or bicyclohexanolmonoalkanols, such as bicyclohexane-4,4'-dimethanol; (e) bridged cyclohexanols, such as hydrogenated bisphenol A (4,4'-isopropylidenediphenol); (f) other cycloaliphatic and polycycloaliphatic diols, monol monoalkanols, or dialkanols such as, cyclopentane-1,3-diol; or (g) aliphatic hydroxyl-containing materials such as alkoxylated phenolic reactants; as described in pages 9 to 15 of co-pending U.S. Patent Application Ser. No. 61/388,059, such pages incorporated herein by reference.

The epichlorohydrin, component (ii); the basic acting substance, component (iii); the non-Lewis acid catalyst, component (iv); and the optional solvent, component (v) useful in the present invention may be selected from the same components as described in pages 15 to 18 of co-pending U.S. Patent Application Ser. No. 61/388,059, such pages incorporated herein by reference.

The recycle process of the present invention includes as a second step a fractionation step including: subjecting the epoxy resin composition produced in step (I) to a fractionation or separation process to remove (A) "light" components such as, for example, solvent used in the epoxidation reaction, if any, unreacted epihalohydrin, and co-products such as di(epoxypropyl)ether; (B) unreacted aliphatic or cycloaliphatic hydroxyl containing material, if any; (C) partially epoxidized aliphatic or cycloaliphatic hydroxyl containing material, such as, for example, MGE; (D) fully epoxidized aliphatic or cycloaliphatic hydroxyl containing material, such as, for example, DGE, such that the (E) PACE resin product remaining contains no more than 50 wt % of said fully epoxidized aliphatic or cycloaliphatic hydroxyl containing material (D).

Most any process or group of processes for the fractionation or separation of the epoxy resin into various components may be employed to provide the MGE or MGE and DGE mixtures for recycle into a fresh epoxidation reaction. Thus, methods such as, for example, vacuum distillation including rotary evaporation, fractional vacuum distillation, short path distillation, packed column distillation, spinning band column distillation, falling film distillation, wiped film distillation, steam distillation, filtration including vacuum filtration, gravity filtration, nanofiltration, microfiltration and ultrafiltration, membrane separations including pervaporation and vapor permeation, centrifugation, water washing or extraction, solvent extraction, supercritical fluid extraction, decantation, column chromatography, electrostatic coalescence, adsorption, and other known fractionation and separation processing methods and the like may be employed. Fractional vacuum distillation is a preferred method for the fractionation of the aliphatic or cycloaliphatic epoxy resin. Falling film distillation and wiped film distillation are likewise preferred methods for fractionation of the epoxy resin.

The recycle process of the present invention includes as a third step a recycle step including: recycling the isolated partially epoxidized aliphatic or cycloaliphatic hydroxyl containing material (C) and any mixtures of partially epoxidized aliphatic or cycloaliphatic hydroxyl containing material (C) with fully epoxidized aliphatic or cycloaliphatic hydroxyl containing material (D) from step (II) to a new reaction mixture of step (I). Thus, if the aliphatic or cycloaliphatic hydroxyl containing material used was a diol, the mixture of partially epoxidized aliphatic or cycloaliphatic hydroxyl containing material which is isolated and recycled into a new epoxidation reaction consists of the corresponding MGE or MGE and DGE mixture. Typically, MGE and DGE mixtures are recycled because fractionation or separation methods typically produce such mixtures. Thus, the partially epoxidized aliphatic or cycloaliphatic hydroxyl containing material may contain 100 wt % MGE to as little as 2 wt % MGE, with the balance consisting of the DGE. It follows that if the aliphatic or cycloaliphatic hydroxyl containing material used was a triol, mixtures of MGE, DGE and triglycidyl ether (TGE) may be used in the recycle process of the present invention.

For the recycle process of the present invention, the point of recycle may be further defined by the extent of conversion of the aliphatic or cycloaliphatic hydroxyl containing materials, by the amount of the various epoxidation products present, the cumulative amount of aqueous alkaline reactant used, or all of these.

Fractions containing unreacted aliphatic or cycloaliphatic hydroxyl containing reactant may additionally be used for the recycle reaction into the fresh epoxidation of step (I). This unreacted aliphatic or cycloaliphatic hydroxyl containing material may be employed as a part of the charge of the aliphatic or cycloaliphatic hydroxyl containing material intended as a reactant in the fresh epoxidation. Thus mixtures of unreacted aliphatic or cycloaliphatic hydroxyl containing material (B) and partially epoxidized aliphatic or cycloaliphatic hydroxyl containing material (C), optionally containing fully epoxidized aliphatic or cycloaliphatic hydroxyl containing material (D) may be recycled to a new reaction mixture of step (I). While typically not preferred, other components may be present as a part of the product to be recycled, for example, one or more solvents which are inert to the epoxidation reaction.

The amount of the recycle MGE or MGE and DGE product used may vary as a function of the composition of said MGE or MGE and DGE product, the structure of the MGE or MGE and DGE product, as well as practical considerations, such as, for example, reactor volume. Thus, from about 0.01 mole to about 2 moles, preferably from about 0.1 mole to about 0.8 mole, most preferably from about 0.2 mole to about 0.5 mole of MGE or combined MGE and DGE per mole of aliphatic or cycloaliphatic reactant used in the epoxidation is typically used in the recycle process.

When the recycle of MGE or MGE and DGE is performed into an epoxidation specifically at the initial stage of aqueous alkaline agent addition in an epoxidation process using 2 or more stages of aqueous alkaline agent addition, increased yields of PACE resin are obtained concurrent with reduced yields of MGE while maintaining DGE yield (overall yield of combined MGE and DGE is reduced). When the recycle of MGE or MGE and DGE is performed into an epoxidation specifically at the final stage of aqueous alkaline agent addition in an epoxidation process using 2 or more stages of aqueous alkaline agent addition, increased yields of DGE are obtained while decreasing the yield of undesirable MGE (overall yield of combined MGE and DGE is maintained) while the yield of PACE resin is decreased.

EXAMPLES

The following Examples and Comparative Examples further illustrate the present invention in detail but are not to be construed to limit the scope thereof.

The following standard abbreviations are used in the Examples and Comparative Examples: "GC" stands for gas chromatography (chromatographic); "MS" stands for mass spectrometry (spectrometric); "EEW" stands for epoxide equivalent weight; "DI" stands for deionized; "eq" stands for equivalent(s); "wt" stands for weight(s); "vol" stands for volume(s); "min" stands for minute(s); "hr" stands for hour(s); "g" stands for gram(s); "mL" stands for milliliter(s); "L" stands for liter(s); "LPM" stands for liter(s) per minute; "µm" stands for micrometer(s); "mm" stands for millimeter(s); "m" stands for meter(s); and "cp" stands for centipoise.

In the following Examples and Comparative Examples, standard analytical equipment and methods are used such as for example, the following:

I.C.I. Cone and Plate Viscosity

Viscosity was determined on an I.C.I. Cone and Plate Viscometer Viscosity (model VR-4540) at 25° C. In the method, the viscometer equipped with a 0-40 poise spindle (model VR-4140) and equilibrated to 25° C. was calibrated to zero then the sample applied and held 2 min with viscosity then checked and the reading taken after 15 seconds. One or more duplicate viscosity tests were completed using a fresh aliquot of the particular product being tested. The individual measurements were averaged.

Percent Epoxide/Epoxide Equivalent Weight Analysis

A standard titration method was used to determine percent epoxide in the various epoxy resins [Jay, R. R., "Direct Titration of Epoxy Compounds and Aziridines", Analytical Chemistry, 36, 3, 667-668 (March, 1964).] In the present adaptation of this method, the carefully weighed sample (sample weight ranges from 0.17-0.25 g) was dissolved in dichloromethane (15 mL) followed by the addition of tetraethylammonium bromide solution in acetic acid (15 mL). The resultant solution treated with 3 drops of crystal violet indicator (0.1% wt/vol in acetic acid) was titrated with 0.1N perchloric acid in acetic acid on a Metrohm 665 Dosimat titrator (Brinkmann). Titration of a blank consisting of dichloromethane (15 mL) and tetraethylammonium bromide solution in acetic acid (15 mL) provided correction for solvent background. Percent epoxide and EEW were calculated using the following equations:

$$\% \text{ Epoxide} = \frac{[(\text{mL titrated sample}) - (\text{mL titrated blank})](0.4303)}{(g \text{ sample titrated})}$$

$$EEW = \frac{4303}{\% \text{ epoxide}}$$

Gas Chromatogaphic Analysis: Area %

In the general method, a Hewlett Packard 5890 Series II Plus gas chromatograph was employed using a DB-1 capillary column (61.4 m by 0.25 mm with a 0.25 μm film thickness, Agilent). The column was maintained in the chromatograph oven at a 50° C. initial temperature. Both the injector inlet and flame ionization detector were maintained at 300° C. Helium carrier gas flow through the column was maintained at 1.1 mL per min. For the analyses of the epoxy resins during synthesis or from the rotary evaporation, an initial 50° C. oven temperature with heating at 12° C. per min to a final temperature of 300° C. revealed that essentially all light boiling components, including residual epichlorohydrin, cyclohexanedimethanols and monoglycidyl ethers of the cyclohexanedimethanols had been removed by the rotary evaporation. For the analyses of the PACE resins, an initial 250° C. oven temperature with heating at 13.3° C. per min to a final temperature of 300° C. was employed for complete elution of all oligomeric components within 50 min total time for the analysis. GC analyses in area % are not a quantitative measure of any given component.

Samples for GC analysis were prepared by collection of a 0.5 mL aliquot of the slurry product from the epoxidation and addition to a vial containing 1 mL of acetonitrile. After shaking to mix, a portion of the slurry in acetonitrile was loaded into a 1 mL syringe (Norm-Ject, all polypropylene/polyethylene, Henke Sass Wolf GmBH) and passed through a syringe filter (Acrodisc CR 13 with 0.2 μm PTFE membrane, Pall Corporation, Gelman Laboratories) to remove inorganic any insoluble debris.

Internally Standardized Gas Chromatographic Analysis for Weight Percent Residual Diglycidyl Ethers of cis-, trans-1,3- and 1,4-Cyclohexanedimethanol in the Polyfunctional Cycloaliphatic Epoxy Resin A single point internal standard method was developed for GC analysis of residual diglycidyl ethers of cis-, trans-1,3- and 1,4-cyclohexanedimethanol remaining in the PACE resin (distillation pot) product. Cyclohexanone was selected as the internal standard since it had a retention time that was different from that of any other components observed in the analyses of the epoxidation products. For the analyses using an internal standard, an initial 50° C. oven temperature with heating at 12° C. per min to a final temperature of 300° C. was employed. For the standard of the diglycidyl ether of cis-, trans-1,3- and 1,4-cyclohexanedimethanol, a distillation cut was employed. This distillation cut contained 0.71 wt % monoglycidyl ethers and 99.29 wt % diglycidyl ethers. A 0.2500 g sample of the standard of the diglycidyl ethers plus 0.7500 g of acetonitrile plus 5 μL of cyclohexanone weighing 0.0047 g. were added to a glass vial. Three separate injections were made in the gas chromatograph and the resultant area counts were averaged for the cyclohexanone and for the diglycidyl ether. This data was used to calculate the internal response factor, as follows:

$$\text{Internal Response Factor} = \frac{(\text{area internal standard})(\text{amount diglycidyl ethers})}{(\text{amount internal standard})(\text{area diglycidyl ethers})}$$

An aliquot (approximately 0.2500 g) of the PACE resin, acetonitrile (approximately 0.7500 g) and cyclohexanone (5 μL, approximately 0.0047 g) were added to a glass vial and analyzed by GC. Using the data from the GC analysis plus the internal response factor, the following calculation was performed:

$$\text{Amount Diglycidyl Ethers} = \frac{(\text{amount internal standard})}{\frac{(\text{area diglycidyl ethers})(\text{Internal Response Factor})}{(\text{area internal standard})}}$$

Comparative Example A

Two Stage Synthesis of Epoxy Resin of cis-, trans-1,3- and 1,4-Cyclohexanedimethanol Epoxidation of cis-, trans-1,3- and 1,4-cyclohexanedimethanol (UNOXOL™ Diol) was performed using two stages of aqueous sodium hydroxide addition followed by fractional vacuum distillation to separate the constituents of the epoxy resin:

A. Epoxidation Reaction

A 5 L, 4 neck, glass, round bottom reactor was charged with UNOXOL™ Diol (432.63 g, 3.0 moles, 6.0 hydroxyl eq), epichlorohydrin (1110.24 g, 12.0 moles, 2:1 epichlorohydrin:UNOXOL™ Diol hydroxyl eq ratio), toluene (2.5 L), and benzyltriethylammonium chloride (43.62 g, 0.1915 mole) in the indicated order. [UNOXOL™ cyclic dialcohol is a registered trademark of Union Carbide Corporation.] The reactor was additionally equipped with a condenser (maintained at 0° C.), a thermometer, a Claisen adaptor, an overhead nitrogen inlet (1 LPM N₂ used), and a stirrer assembly (Teflon™ paddle, glass shaft, variable speed motor). [Teflon™ fluorocarbon resin is a trademark of E.I. duPont de Nemours.] A controller monitored the temperature registered on the thermometer in the reactor and provided heating via the heating mantle placed under the reactor as well as cooling delivered by a pair of fans positioned on the reactor exterior. Sodium hydroxide (360.0 g, 9.0 moles) dissolved in DI water (360 g) for the initial addition was added to a side arm vented addition funnel, sealed with a ground glass stopper, then attached to the reactor. Stirring commenced to give a 25° C. mixture followed by commencement of dropwise addition of the aqueous sodium hydroxide solution. The reaction mixture was allowed to self-heat to 40° C. during the aqueous sodium hydroxide addition time and then held at that temperature via cooling from the fans as needed. Thus, after 130 min, 42.3% of the aqueous sodium hydroxide was added causing the reaction temperature to first reach 39-40° C. and then remain at that temperature range for the remainder of the aqueous sodium hydroxide addition. Addition of the aqueous sodium hydroxide required a total of 248 min. After 16 hr of postreaction the temperature had declined to 26° C., stirring ceased, and the reactor contents allowed to settle. The organic layer was decanted from the reactor followed by addition of 1.5 L of DI water to the salt and residual toluene left behind in the reactor. After addition into a 2 L separatory funnel and settling, the toluene layer which separated from the aqueous salt solution was recovered and combined back with the decanted organic layer. The aqueous layer was discarded as waste. GC analysis after normalization to remove solvents (acetonitrile and toluene) and unreacted epichlorohydrin revealed the presence of 4.51 area % light components, 2.32 area % unreacted cis-, trans-1,3- and 1,4-cyclohexanedimethanol; 43.14 area % monoglycidyl ethers, 0.14 area % of a pair of components associated with the diglycidyl ether peaks, 45.83 area % diglycidyl ethers, and 4.06 area % oligomers that were volatile under the conditions of the GC analysis.

The organic layer was reloaded into the reactor along with fresh benzyltriethylammonium chloride (21.81 g, 0.1915 mole). Sodium hydroxide (180 g, 4.5 moles) dissolved in DI water (180 g) was added to a side arm vented addition funnel, sealed with a ground glass stopper, then attached to the reactor. Stirring commenced to give a 24° C. mixture followed by commencement of dropwise addition of the aqueous sodium hydroxide solution. The reaction mixture was allowed to self-heat during the aqueous sodium hydroxide addition time. Thus, after 120 min 100% of the aqueous sodium hydroxide was added causing the reaction temperature to reach a maximum of 34.5° C. After 16.2 hr of postreaction the temperature had declined to 24° C., stirring ceased, and the reactor contents allowed to settle. The organic layer was decanted from the reactor followed by addition of 1.0 L of DI water to the salt and residual toluene left behind in the reactor. After addition into a 2 L separatory funnel and settling, the toluene layer which separated from the aqueous salt solution was recovered and combined back with the decanted organic layer. The aqueous layer was discarded as waste. GC analysis after normalization to remove solvents (acetonitrile and toluene) and unreacted epichlorohydrin revealed the presence of 5.16 area % light components, 0.27 area % unreacted cis-, trans-1,3- and 1,4-cyclohexanedimethanol; 13.64 area % monoglycidyl ethers, 0.26 area % of a pair of components associated with the diglycidyl ether peaks, 73.68 area % diglycidyl ethers, and 6.99 area % oligomers that were volatile under the conditions of the GC analysis.

B. Epoxy Resin Product Isolation

After removal of the aqueous layer from the reaction with the second aqueous sodium hydroxide addition, the organic layer was equally split between the pair of separatory funnels and the contents of each respective separatory funnel then washed with DI water (400 mL) by vigorously shaking. The washed product was allowed to settle for 2 hr, and then the aqueous layer was removed and discarded as waste. A second wash was completed using the aforementioned method, with settling overnight (20 hr) required to fully resolve the organic and aqueous layers. The combined, hazy organic solution was filtered through a bed of anhydrous, granular sodium sulfate in a 600 mL fritted glass funnel providing a transparent filtrate.

Rotary evaporation of the filtrate using a maximum oil bath temperature of 106° C. to a final vacuum of 2.4 mm of Hg removed the bulk of the volatiles. A total of 731.45 g of light yellow colored, transparent liquid was recovered after completion of the rotary evaporation. GC analysis after normalization to remove solvent (acetonitrile) revealed the presence of 14.37 area % monoglycidyl ethers, 0.20 area % of a pair of components associated with the diglycidyl ether peaks, 81.98 area % diglycidyl ethers, and 3.45 area % oligomers that were volatile under the conditions of the GC analysis. Thus, GC analysis revealed that essentially all light boiling components, including residual epichlorohydrin, had been removed.

C. Fractional Vacuum Distillation

A portion (730.72 g) of the product from the rotary evaporation was added to a 1 L, 3 neck, glass, round bottom reactor equipped with magnetic stiffing and a thermometer for monitoring the pot temperature. A one piece integral vacuum jacketed Vigreux distillation column and head was attached to the reactor. The distillation column nominally provided 9 to 18 theoretical plates depending on the mode of operation. The distillation head was equipped with an overhead thermometer, air cooled condenser, a receiver and a vacuum takeoff. A vacuum pump was employed along with a liquid nitrogen trap and an in-line digital thermal conductivity vacuum gauge. Stiffing commenced followed by application of full vacuum then progressively increased heating using a thermostatically controlled heating mantle. A clean receiver was used to collect each respective distillation cut. During the distillation, the initial distillation cuts were taken to sequentially remove all components boiling below the cyclohexanedimethanols, all unreacted cyclohexanedimethanols, and the bulk of the monoglycidyl ethers. GC analysis was conducted on each fraction collected from the distillation to give MGE and DGE wt %. Total amounts of MGE and DGE were used to calculate respective yields based on cis-, trans-1,3- and 1,4-cyclohexanedimethanol reactant with the results shown in Table I. The final distillation cuts sought to selectively remove diglycidyl ether, leaving the oligomeric product (215.32 g) in the distillation pot. Normalization with respect to the total epoxy resin recovered from the rotary evaporation indicated 215.54 g of oligomers. GC analysis using a cyclohexanone internal standard revealed that the oligomers contained residual 5.51 wt % diglycidyl ether with the balance as the oligomers. After removal of the weight contributed by the residual DGE, the normalized weight of DGE-free oligomers was 203.66 g. After normalization to remove the peaks associated with acetonitrile solvent and the diglycidyl ether, the GC analysis demonstrated the following oligomeric components containing multiple isomers:

4.52 area % 2-propanol, 1-(oxiranylmethoxy)-3-[[3(or 4)-[(oxiranylmethoxy)methyl]cyclohexyl]methoxy]- and oxirane, 2-[[2-chloro-1-[[[3(or 4)-[(oxiranylmethoxy)methyl]cyclohexyl]methoxy]methyl]ethoxy]methyl]-

20.39 area % oxirane, 2-[[[3(or 4)-[[2,3-bis(oxiranylmethoxy)propoxy]methyl]cyclohexyl]methoxy]methyl]-

1.44 area % cyclohexanemethanol, 3(or 4)-[[2-hydroxy-3-[[3 (or 4)-[(oxiranylmethoxy)methyl]cyclohexyl]methoxy] propoxy]methyl]-

22.03 area % 2-propanol, 1,3-bis[[3(or 4)-[(oxiranylmethoxy)methyl]cyclohexyl]methoxy]-

51.62 area % oxirane, 2-[[2-[[3(or 4)-[(oxiranylmethoxy)methyl]cyclohexyl]methoxy]-1-[[[3(or 4)-[(oxiranylmethoxy)methyl]cyclohexyl]methoxy]methyl]ethoxy]methyl]-

Titration demonstrated an EEW of 197.1. I.C.I. cone and plate viscosity was 3472 cp.

Example 1

Two Stage Synthesis of Epoxy Resin of cis-, trans-1,3 and 1,4-Cyclohexanedimethanol with Recycle of Monoglycidyl Ether and Diglycidyl Ether of cis-, trans-1,3 and 1,4-Cyclohexanedimethanol in Stage 1

Epoxidation of cis-, trans-1,3- and 1,4-cyclohexanedimethanol (UNOXOL™ Diol) was performed using two stages of aqueous sodium hydroxide addition with recycle of MGE and DGE of cis-, trans-1,3- and 1,4-cyclohexanedimethanol in the first stage followed by fractional vacuum distillation to separate the constituents of the epoxy resin:

A. Epoxidation Reaction

A 5 L, 4 neck, glass, round bottom reactor was charged with UNOXOL™ Diol (432.63 g, 3.0 moles, 6.0 hydroxyl eq), epichlorohydrin (1110.24 g, 12.0 moles, 2:1 epichlorohydrin:UNOXOL™ Diol hydroxyl eq ratio), toluene (2.5 L), benzyltriethylammonium chloride (43.62 g, 0.1915 mole), and a recycle stream consisting of monoglycidyl ether of cis-, trans-1,3- and 1,4-cyclohexanedimethanol (63.42 g, 0.3167 mole) and diglycidyl ether of cis-, trans-1,3- and 1,4-cyclohexanedimethanol (150.88 g, 0.5886 mole) in the indicated order. The reactor was additionally equipped as specified in Comparative Example A above. Sodium hydroxide (360.0 g, 9.0 moles) dissolved in DI water (360 g) for the initial addition was added to a side arm vented addition funnel, sealed with a ground glass stopper, then attached to the reactor. Stirring commenced to give a 22° C. mixture followed by commencement of dropwise addition of the aqueous sodium hydroxide solution. The reaction mixture was allowed to self-heat to 40° C. during the aqueous sodium hydroxide addition time and then held at that temperature via cooling from the fans as needed. Thus, after 92 min, 43.2% of the aqueous sodium hydroxide was added causing the reaction temperature to first reach 39-40° C. and then remain at that temperature range for the remainder of the aqueous sodium hydroxide addition. Addition of the aqueous sodium hydroxide required a total of 222 min After 15.8 hr of postreaction the temperature had declined to 27.5° C., stirring ceased, and the reactor contents allowed to settle. The organic layer was decanted from the reactor and processed as specified in Comparative Example A above. GC analysis after normalization to remove solvents (acetonitrile and toluene) and unreacted epichlorohydrin revealed the presence of 2.91 area % light components, 2.15 area % unreacted cis-, trans-1,3- and 1,4-cyclohexanedimethanol; 36.05 area % monoglycidyl ethers, 0.17 area % of a pair of components associated with the diglycidyl ether peaks, 56.34 area % diglycidyl ethers, and 2.38 area % oligomers that were volatile under the conditions of the GC analysis.

The organic layer was reloaded into the reactor along with fresh benzyltriethylammonium chloride (21.81 g, 0.1915 mole). Sodium hydroxide (180 g, 4.5 moles) dissolved in DI water (180 g) was added to a side arm vented addition funnel, sealed with a ground glass stopper, then attached to the reactor. Stirring commenced to give a 24° C. mixture followed by commencement of dropwise addition of the aqueous sodium hydroxide solution. The reaction mixture was allowed to self-heat during the aqueous sodium hydroxide addition time. Thus, after 135 min 100% of the aqueous sodium hydroxide was added causing the reaction temperature to reach a maximum of 34.5° C. After 16.35 hr of postreaction the temperature had declined to 24° C., stirring ceased, and the reactor contents allowed to settle. The organic layer was decanted from the reactor and processed as specified in Comparative Example A above. GC analysis after normalization to remove solvents (acetonitrile and toluene) and unreacted epichlorohydrin revealed the presence of 6.73 area % light components, 0.29 area % unreacted cis-, trans-1,3- and 1,4-cyclohexanedimethanol; 12.95 area % monoglycidyl ethers, 0.29 area % of a pair of components associated with the diglycidyl ether peaks, 77.55 area % diglycidyl ethers, and 2.19 area % oligomers that were volatile under the conditions of the GC analysis.

B. Epoxy Resin Product Isolation

The aqueous layer from the reaction was processed as specified in Comparative Example A above. Rotary evaporation of the filtrate using a maximum oil bath temperature of 100° C. to a final vacuum of 2.7 mm of Hg removed the bulk of the volatiles. A total of 964.46 g of light yellow colored, transparent liquid was recovered after completion of the rotary evaporation. GC analysis after normalization to remove solvent (acetonitrile) revealed the presence of 12.58 area % monoglycidyl ethers, 0.24 area % of a pair of components associated with the diglycidyl ether peaks, 83.12 area % diglycidyl ethers, and 4.06 area % oligomers that were volatile under the conditions of the GC analysis. Thus, GC analysis revealed that essentially all light boiling components, including residual epichlorohydrin, had been removed.

C. Fractional Vacuum Distillation

A portion (964.27 g) of the product from the rotary evaporation was processed as specified in Comparative Example A above. The amounts of MGE and DGE after removal of the amounts of MGE and DGE charged in the recycle step were used to calculate respective yields based on cis-, trans-1,3- and 1,4-cyclohexanedimethanol reactant with the results shown in Table I. The final distillation cuts sought to selectively remove diglycidyl ether, leaving the oligomeric product (283.86 g) in the distillation pot. Normalization with respect to the total epoxy resin recovered from the rotary evaporation indicated 283.92 g of oligomers. GC analysis using a cyclohexanone internal standard revealed that the oligomers contained residual 7.67 wt % diglycidyl ether with the balance as the oligomers. After removal of the weight contributed by the residual DGE, the normalized weight of DGE-free oligomers was 262.14 g. After normalization to remove the peaks associated with acetonitrile solvent and the diglycidyl ether, the GC analysis demonstrated the following oligomeric components containing multiple isomers:

2.97 area % 2-propanol, 1-(oxiranylmethoxy)-3-[[3(or 4)-[(oxiranylmethoxy)methyl]cyclohexyl]methoxy]-
and
oxirane, 2-[[2-chloro-1-[[[3(or 4)-[(oxiranylmethoxy)methyl]cyclohexyl]methoxy]methyl]ethoxy]methyl]-

18.91 area % oxirane, 2-[[[3(or 4)-[[2,3-bis(oxiranylmethoxy)propoxy]methyl]cyclohexyl]methoxy]methyl]-

2.31 area % cyclohexanemethanol, 3(or 4)-[[2-hydroxy-3-[[3(or 4)-[(oxiranylmethoxy)methyl]cyclohexyl]methoxy]propoxy]methyl]-

27.24 area % 2-propanol, 1,3-bis[[3(or 4)-[(oxiranylmethoxy)methyl]cyclohexyl]methoxy]-

48.57 area % oxirane, 2-[[2-[[3(or 4)-[(oxiranylmethoxy)methyl]cyclohexyl]methoxy]-1-[[[3(or 4)-[(oxiranylmethoxy)methyl]cyclohexyl]methoxy]methyl]ethoxy]methyl]-

Titration demonstrated an EEW of 198.1. I.C.I. cone and plate viscosity was 3316 cp.

TABLE I

| PROPERTY | Example 1 (2-Stage Epoxidation with MGE/DGE Recycle) | Comparative Example A (2-Stage Epoxidation) |
|---|---|---|
| CHDM Conversion (%) | >99.95 | >99.95 |
| MGE Yield (%) | 5.1 | 11.7 |
| DGE Yield (%) | 59.0 | 58.6 |
| Combined MGE/DGE Yield (%) | 64.1 | 70.3 |
| DGE Residual in Pot (% wt.) | 7.67 | 5.51 |
| Pot (PACE resin)Less Residual DGE (g) | 262.14 | 203.66 |
| EEW PACE Resin | 198.1 | 197.1 |
| I.C.I. Cone and Plate Viscosity PACE Resin (cp/25° C.) | 3316 | 3472 |

Comparison of the data given in Table I demonstrates the beneficial effect of recycle of MGE and DGE containing fractions isolated from the epoxy resin of an aliphatic or cycloaliphatic epoxy resin into an epoxidation specifically at the initial stage of aqueous alkaline agent addition. Increased yield (262.14 g with recycle versus 203.66 g without recycle) of PACE resin is obtained concurrent with reduced yields of MGE (5.1% yield with recycle versus 11.7% yield without recycle) while maintaining DGE yield (58.6% yield with recycle versus 59.0% yield without recycle). Examination of the GC MS data given for the respective oligomeric components in Comparative Example A versus Example 1 shows that the composition of this PACE resin is substantially maintained in the recycle process and no new components are detected as a result of the recycle process.

Comparative Example B

Three Stage Synthesis of Epoxy Resin of cis-, trans-1,3- and 1,4-Cyclohexanedimethanol Epoxidation of cis-, trans-1,3- and 1,4-cyclohexanedimethanol (UNOXOL™ Diol) was performed using three stages of aqueous sodium hydroxide followed by fractional vacuum distillation to separate the constituents of the epoxy resin:

A. Epoxidation Reaction

A 5 L, 4 neck, glass, round bottom reactor was charged with UNOXOL™ Diol (432.63 g, 3.0 moles, 6.0 hydroxyl eq), epichlorohydrin (1110.24 g, 12.0 moles, 2:1 epichlorohydrin:UNOXOL™ Diol hydroxyl eq ratio), toluene (2.5 L), and benzyltriethylammonium chloride (43.62 g, 0.1915 mole) in the indicated order. The reactor was additionally equipped as specified in Comparative Example A above. Sodium hydroxide (360.0 g, 9.0 moles) dissolved in DI water (360 g) for the initial addition was added to a side arm vented addition funnel, sealed with a ground glass stopper, then attached to the reactor. Stirring commenced to give a 21° C. mixture followed by commencement of dropwise addition of the aqueous sodium hydroxide solution. The reaction mixture was allowed to self-heat to 40° C. during the aqueous sodium hydroxide addition time and then held at that temperature via cooling from the fans as needed. Thus, after 55 min, 25% of the aqueous sodium hydroxide was added causing the reaction temperature to first reach 39-40° C. and then remain at that temperature range for the remainder of the aqueous sodium hydroxide addition. Addition of the aqueous sodium hydroxide required a total of 280 min After 14.3 hr of postreaction the temperature had declined to 30° C., stirring ceased, and the reactor contents allowed to settle. The organic layer was decanted from the reactor and processed as specified in Comparative Example A above. GC analysis after normalization to remove solvents (acetonitrile and toluene) and unreacted epichlorohydrin revealed the presence of 2.44 area % light components, 2.79 area % unreacted cis-, trans-1,3- and 1,4-cyclohexanedimethanol; 39.77 area % monoglycidyl ethers, 0.12 area % of a pair of components associated with the diglycidyl ether peaks, 50.91 area % diglycidyl ethers, and 3.73 area % oligomers that were volatile under the conditions of the GC analysis.

The organic layer was reloaded into the reactor along with fresh benzyltriethylammonium chloride (21.81 g, 0.1915 mole). Sodium hydroxide (180 g, 4.5 moles) dissolved in DI water (180 g) was added to a side arm vented addition funnel, sealed with a ground glass stopper, then attached to the reactor. Stirring commenced to give a 23.5° C. mixture followed by commencement of dropwise addition of the aqueous sodium hydroxide solution. The reaction mixture was allowed to self-heat during the aqueous sodium hydroxide addition time. Thus, after 105 min 91.7% of the aqueous sodium hydroxide was added causing the reaction temperature to reach a maximum of 39° C. and then remain at that temperature range for the remainder of the aqueous sodium hydroxide addition. After 16.2 hr of postreaction the temperature had declined to 24° C., stirring ceased, and the reactor contents allowed to settle. The organic layer was decanted from the reactor and processed as specified in Comparative Example 1 above. GC analysis after normalization to remove solvents (acetonitrile and toluene) and unreacted epichlorohydrin revealed the presence of 3.02 area % light components, 0.22 area % unreacted cis-, trans-1,3- and 1,4-cyclohexanedimethanol; 10.83 area % monoglycidyl ethers, 0.26 area % of a pair of components associated with the diglycidyl ether peaks, 79.56 area % diglycidyl ethers, and 5.96 area % oligomers that were volatile under the conditions of the GC analysis.

The organic layer was reloaded into the reactor along with fresh benzyltriethylammonium chloride (10.91 g, 0.0958 mole). Sodium hydroxide (90 g, 2.25 moles) dissolved in DI water (90 g) was added to a side arm vented addition funnel, sealed with a ground glass stopper, then attached to the reactor. Stirring commenced to give a 24° C. mixture followed by commencement of dropwise addition of the aqueous sodium hydroxide solution. The reaction mixture was allowed to self-heat during the aqueous sodium hydroxide addition time. Thus, after 25 min 37.5% of the aqueous sodium hydroxide was added causing the reaction temperature to reach a maximum of 25° C. and then remain at that temperature range for the remainder of the aqueous sodium hydroxide addition. After 17.0 hr of postreaction the temperature had declined to 23° C., stirring ceased, and the reactor contents allowed to settle. The organic layer was decanted from the reactor and processed as specified in Comparative Example A above. GC analysis after normalization to remove solvents (acetonitrile and toluene) and unreacted epichlorohydrin revealed the presence of 4.28 area % light components, 0.03 area % unreacted cis-, trans-1,3- and 1,4-cyclohexanedimethanol; 4.93 area % monoglycidyl ethers, 0.28 area % of a pair of components associated with the diglycidyl ether peaks, 81.47 area % diglycidyl ethers, and 8.85 area % oligomers that were volatile under the conditions of the GC analysis.

B. Epoxy Resin Product Isolation

The aqueous layer from the reaction was processed as specified in Comparative Example A above. Rotary evaporation of the filtrate using a maximum oil bath temperature of 100° C. to a final vacuum of 4.1 mm of Hg removed the bulk of the volatiles. A total of 742.92 g of light yellow colored, transparent liquid was recovered after completion of the rotary evaporation. GC analysis after normalization to remove solvent (acetonitrile) revealed the presence of 4.84 area % monoglycidyl ethers, 0.51 area % of a pair of components associated with the diglycidyl ether peaks, 88.00 area % diglycidyl ethers, and 6.61 area % oligomers that were volatile under the conditions of the GC analysis. Thus, GC analysis revealed that essentially all light boiling components, including residual epichlorohydrin, had been removed.

C. Fractional Vacuum Distillation

A portion (741.62 g) of the product from the rotary evaporation was processed as specified in Comparative Example A above. The final distillation cuts sought to selectively remove diglycidyl ether, leaving the oligomeric product (238.98 g) in the distillation pot. The oligomeric product was dissolved in dichloromethane (250 mL) and then added to a separatory funnel and washed with DI water (100 mL). The organic solution recovered from the separatory funnel was dried over anhydrous sodium sulfate and filtered through a medium fritted glass funnel. Rotary evaporation of the filtrate using a maximum oil bath temperature of 100° C. to a final vacuum of 5.7 mm of Hg removed the dichloromethane. After cooling to 25° C., the oligomeric product was filtered over a bed of diatomaceous earth packed in a medium fritted glass funnel to provide a transparent, yellow liquid. GC analysis using a cyclohexanone internal standard revealed that the oligomers contained residual 6.60 wt % diglycidyl ether with the balance as the oligomers. After normalization to remove the peaks associated with acetonitrile solvent and the diglycidyl ether, the GC analysis demonstrated the following oligomeric components containing multiple isomers:

3.16 area % 2-propanol, 1-(oxiranylmethoxy)-3-[[3(or 4)-[(oxiranylmethoxy)methyl]cyclohexyl]methoxy]- and oxirane, 2-[[2-chloro-1-[[[3(or 4)-[(oxiranylmethoxy)methyl]cyclohexyl]methoxy]methyl]ethoxy]methyl]-

23.47 area % oxirane, 2-[[[3(or 4)-[[2,3-bis(oxiranylmethoxy)propoxy]methyl]cyclohexyl]methoxy]methyl]-

0.27 area % cyclohexanemethanol, 3(or 4)-[[2-hydroxy-3-[[3 (or 4)-[(oxiranylmethoxy)methyl]cyclohexyl]methoxy] propoxy]methyl]-

12.56 area % 2-propanol, 1,3-bis[[3(or 4)-[(oxiranylmethoxy)methyl]cyclohexyl]methoxy]-

60.54 area % oxirane, 2-[[2-[[3(or 4)-[(oxiranylmethoxy)methyl]cyclohexyl]methoxy]-1-[[[3(or 4)-[(oxiranylmethoxy)methyl]cyclohexyl]methoxy]methyl]ethoxy] methyl]-

Titration demonstrated an EEW of 187.3. I.C.I. cone and plate viscosity was 2946 cp.

Example 2

Three Stage Synthesis of Epoxy Resin of cis-, trans-1,3- and 1,4-Cyclohexanedimethanol with Recycle of Monoglycidyl Ether and Diglycidyl Ether of cis-, trans-1,3- and 1,4-Cyclohexanedimethanol in Stage 3

Epoxidation of cis-, trans-1,3- and 1,4-cyclohexanedimethanol (UNOXOL™ Diol) was performed using three stages of aqueous sodium hydroxide addition with recycle of MGE and DGE of cis-, trans-1,3- and 1,4-cyclohexanedimethanol in the third stage followed by fractional vacuum distillation to separate the constituents of the epoxy resin:

A. Epoxidation Reaction

A 5 L, 4 neck, glass, round bottom reactor was charged with UNOXOL™ Diol (432.63 g, 3.0 moles, 6.0 hydroxyl eq), epichlorohydrin (1110.24 g, 12.0 moles, 2:1 epichlorohydrin:UNOXOL™ Diol hydroxyl eq ratio), toluene (2.5 L), and benzyltriethylammonium chloride (43.62 g, 0.1915 mole) in the indicated order. The reactor was additionally equipped as specified in Comparative Example A above. Sodium hydroxide (360.0 g, 9.0 moles) dissolved in DI water (360 g) for the initial addition was added to a side arm vented addition funnel, sealed with a ground glass stopper, then attached to the reactor. Stirring commenced to give a 21.5° C. mixture followed by commencement of dropwise addition of the aqueous sodium hydroxide solution. The reaction mixture was allowed to self-heat to 40° C. during the aqueous sodium hydroxide addition time and then held at that temperature via cooling from the fans as needed. Thus, after 182 min, 75.0% of the aqueous sodium hydroxide was added causing the reaction temperature to first reach 39-40° C. and then remain at that temperature range for the remainder of the aqueous sodium hydroxide addition. Addition of the aqueous sodium hydroxide required a total of 252 min After 14.8 hr of postreaction the temperature had declined to 24.5° C., stirring ceased, and the reactor contents allowed to settle. The organic layer was decanted from the reactor and processed as specified in Comparative Example A above. GC analysis after normalization to remove solvents (acetonitrile and toluene) and unreacted epichlorohydrin revealed the presence of 5.08 area % light components, 2.51 area % unreacted cis-, trans-1,3- and 1,4-cyclohexanedimethanol; 42.83 area % monoglycidyl ethers, 0.20 area % of a pair of components associated with the diglycidyl ether peaks, 46.11 area % diglycidyl ethers, and 3.27 area % oligomers that were volatile under the conditions of the GC analysis.

The organic layer was reloaded into the reactor along with fresh benzyltriethylammonium chloride (21.81 g, 0.0958 mole). Sodium hydroxide (180 g, 4.5 moles) dissolved in DI water (180 g) was added to a side arm vented addition funnel, sealed with a ground glass stopper, then attached to the reactor. Stirring commenced to give a 23.5° C. mixture followed by commencement of dropwise addition of the aqueous sodium hydroxide solution. The reaction mixture was allowed to self-heat during the aqueous sodium hydroxide addition time. Thus, after 88 min 62.5% of the aqueous sodium hydroxide was added causing the reaction temperature to reach a maximum of 31° C. Addition of the aqueous sodium hydroxide required a total of 195 min After 14.75 hr of postreaction the temperature had declined to 22° C., stirring ceased, and the reactor contents allowed to settle. The organic layer was decanted from the reactor and processed as specified in Comparative Example A above. GC analysis after normalization to remove solvents (acetonitrile and toluene) and unreacted epichlorohydrin revealed the presence of 4.45 area % light components, 0.22 area % unreacted cis-, trans-1,3- and 1,4-cyclohexanedimethanol; 14.35 area % monoglycidyl ethers, 0.36 area % of a pair of components associated with the diglycidyl ether peaks, 77.41 area % diglycidyl ethers, and 3.21 area % oligomers that were volatile under the conditions of the GC analysis.

The organic layer was reloaded into the reactor along with fresh benzyltriethylammonium chloride (10.91 g, 0.0958 mole) and a recycle stream consisting of MGE of cis-, trans-1,3- and 1,4-cyclohexanedimethanol (27.98 g, 0.1397 mole)

and DGE of cis-, trans-1,3- and 1,4-cyclohexanedimethanol (162.66 g, 0.6346 mole), in the indicated order. Sodium hydroxide (90 g, 2.25 moles) dissolved in DI water (90 g) was added to a side arm vented addition funnel, sealed with a ground glass stopper, then attached to the reactor. Stirring commenced to give a 25° C. mixture followed by commencement of dropwise addition of the aqueous sodium hydroxide solution. The reaction mixture was allowed to self-heat during the aqueous sodium hydroxide addition time, maintaining the reaction temperature of 25° C. for the entire aqueous sodium hydroxide addition. Addition of the aqueous sodium hydroxide required a total of 60 min After 52 min of post reaction, the reaction temperature reached a maximum of 26° C. After 17.1 hr of postreaction the temperature had declined to 22.5° C., stirring ceased, and the reactor contents allowed to settle. The organic layer was decanted from the reactor and processed as specified in Comparative Example A above. GC analysis after normalization to remove solvents (acetonitrile and toluene) and unreacted epichlorohydrin revealed the presence of 4.93 area % light components, no detected unreacted cis-, trans-1,3- and 1,4-cyclohexanedimethanol; 5.07 area % monoglycidyl ethers, 0.52 area % of a pair of components associated with the diglycidyl ether peaks, 84.87 area % diglycidyl ethers, and 4.61 area % oligomers that were volatile under the conditions of the GC analysis.

B. Epoxy Resin Product Isolation

The aqueous layer from the reaction was processed as specified in Comparative Example A above. Rotary evaporation of the filtrate using a maximum oil bath temperature of 100° C. to a final vacuum of 2.95 mm Hg removed the bulk of the volatiles. A total of 942.10 g of light yellow colored, transparent liquid was recovered after completion of the rotary evaporation. GC analysis after normalization to remove solvent (acetonitrile) revealed the presence of 5.38 area % monoglycidyl ethers, 0.40 area % of a pair of components associated with the diglycidyl ether peaks, 89.44 area % diglycidyl ethers, and 4.76 area % oligomers that were volatile under the conditions of the GC analysis. Thus, GC analysis revealed that essentially all light boiling components, including residual epichlorohydrin, had been removed.

C. Fractional Vacuum Distillation

A portion (940.58 g) of the product from the rotary evaporation was processed as specified in Comparative Example A above. The amounts of MGE and DGE after removal of the amounts of MGE and DGE charged in the recycle step were used to calculate respective yields based on cis-, trans-1,3- and 1,4-cyclohexanedimethanol reactant with the results shown in Table II. The final distillation cuts sought to selectively remove diglycidyl ether, leaving the oligomeric product (231.46 g) in the distillation pot. Normalization with respect to the total epoxy resin recovered from the rotary evaporation indicated 231.83 g of oligomers. The profile of the entire distillation process is summarized in Appendix IV. GC analysis was conducted on each fraction collected from the distillation to give MGE and DGE wt %. GC analysis using a cyclohexanone internal standard revealed that the oligomers contained residual 4.85 wt % diglycidyl ether with the balance as the oligomers. After removal of the weight contributed by the residual DGE, the normalized weight of DGE-free oligomers was 220.59 g. After normalization to remove the peaks associated with acetonitrile solvent and the diglycidyl ether, the GC analysis demonstrated the following oligomeric components containing multiple isomers:

2.89 area % 2-propanol, 1-(oxiranylmethoxy)-3-[[3(or 4)-[(oxiranylmethoxy)methyl]cyclohexyl]methoxy]- and oxirane, 2-[[2-chloro-1-[[[3(or 4)-[(oxiranylmethoxy)methyl]cyclohexyl]methoxy]methyl]ethoxy]methyl]-

19.16 area % oxirane, 2-[[[3(or 4)-[[2,3-bis(oxiranylmethoxy)propoxy]methyl]cyclohexyl]methoxy]methyl]-

0.24 area % cyclohexanemethanol, 3(or 4)-[[2-hydroxy-3-[[3 (or 4)-[(oxiranylmethoxy)methyl]cyclohexyl]methoxy]propoxy]methyl]-

12.84 area % 2-propanol, 1,3-bis[[3(or 4)-[(oxiranylmethoxy)methyl]cyclohexyl]methoxy]-

64.87 area % oxirane, 2-[[2-[[3(or 4)-[(oxiranylmethoxy)methyl]cyclohexyl]methoxy]-1-[[[3(or 4)-[(oxiranylmethoxy)methyl]cyclohexyl]methoxy]methyl]ethoxy]methyl]-

Titration demonstrated an EEW of 188.1. I.C.I. cone and plate viscosity was 3104 cp.

TABLE II

| PROPERTY | Example 2 (3-Stage Epoxidation with MGE/DGE Recycle) | Comparative Example B (3-Stage Epoxidation) |
| --- | --- | --- |
| CHDM Conversion (%) | 100 | 100 |
| MGE Yield (%) | 2.52 | 5.81 |
| DGE Yield (%) | 68.45 | 65.53 |
| Combined MGE/DGE Yield (%) | 70.97 | 71.34 |
| DGE Residual in Pot (% wt.) | 4.85 | 5.55 |
| Pot Less Residual DGE (g) | 220.23 | 235.00 |
| EEW PACE Resin | 188.1 | 187.3 |
| I.C.I. Cone and Plate Viscosity PACE Resin (cp/25° C.) | 3104 | 2946 |

Comparison of the data given in Table II demonstrates the beneficial effect of recycle of MGE and DGE containing fractions isolated from the epoxy resin of an aliphatic or cycloaliphatic epoxy resin into an epoxidation specifically at the final stage of aqueous alkaline agent addition. Decreased yield (220.23 g with recycle versus 235.00 g without recycle) of PACE resin is obtained concurrent with reduced yields of MGE (2.52% yield with recycle versus 5.81% yield without recycle) while increasing DGE yield (68.45% yield with recycle versus 65.53% yield without recycle). Examination of the GC and MS data given for the respective oligomeric components in Comparative Example B versus Example 2 shows that the composition of the PACE resin is substantially maintained in the recycle process and no new components are detected as a result of the recycle process.

What is claimed is:

1. A process for preparing an aliphatic or cycloaliphatic epoxy resin comprising the steps of:
    (I) reacting a mixture of (i) an aliphatic or cycloaliphatic hydroxyl containing material, (ii) an epihalohydrin, (iii) a basic acting substance, (iv) a non-Lewis acid catalyst, and (v) optionally, a solvent, forming an epoxy resin composition;
    (II) subjecting the epoxy resin composition produced in step (I) to a separation process to produce at least the following fractions: (A) a fraction of "light" components, if any; (B) a fraction of unreacted aliphatic or cycloaliphatic hydroxyl containing material, if any; (C) a fraction of partially epoxidized aliphatic or cycloaliphatic hydroxyl containing material; (D) a fraction of fully epoxidized aliphatic or cycloaliphatic hydroxyl containing material; and (E) a fraction of an oligomeric polyfunctional aliphatic or cycloaliphatic epoxy resin material; and
    (III) recycling, optionally with addition of an inert solvent,
        (a) the isolated partially epoxidized aliphatic or cycloaliphatic hydroxyl containing material, component (C), and/or (b) a mixture of partially epoxidized aliphatic or cycloaliphatic hydroxyl containing material (C) and fully epoxidized aliphatic or cycloaliphatic hydroxyl containing material, component (D) and/or (c) a mixture of unreacted aliphatic or cycloaliphatic hydroxyl containing material, component (B) and component (C) and/or (d) a mixture of components (B), (C) and (D) from step (II) to the reaction mixture of step (I).

2. The process of claim 1, wherein recycle of monoglycidyl ether and/or monoglycidyl ether and diglycidyl ether fractions isolated from the epoxy resin of an aliphatic or cycloaliphatic epoxy resin is performed into an epoxidation specifically at the initial stage of aqueous alkaline agent addition in an epoxidation process using two or more stages of aqueous alkaline agent addition.

3. The process of claim 1, wherein recycle of monoglycidyl ether and/or monoglycidyl ether and diglycidyl ether fractions isolated from the epoxy resin of an aliphatic or cycloaliphatic epoxy resin is performed into an epoxidation specifically at the final stage of aqueous alkaline agent addition in an epoxidation process using two or more stages of aqueous alkaline agent addition.

4. The process of claim 1, wherein the aliphatic or cycloaliphatic hydroxyl containing material comprises one or more cyclohexanedialkanols, cyclohexenedialkanols, cyclohexanolmonoalkanols, cyclohexenolmonoalkanols, decahydronaphthalenedialkanols, octahydronaphthalenedialkanols; 1,2,3,4-tetrahydronaphthalenedialkanols; or bridged cyclohexanols.

5. The process of claim 4, wherein the cycloaliphatic hydroxyl containing material may additionally be selected from the group consisting of cycloaliphatic or polycycloaliphatic diols, monol monoalkanols or dialkanols including the dicyclopentadienedimethanols, the norbornenedimethanols, the norbornanedimethanols, the cyclooctanedimethanols, the cyclooctenedimethanols, the cyclooctadienedimethanols, the pentacyclodecanedimethanols, the bicyclooctanedimethanols, the tricyclodecanedimethanols, the bicycloheptenedimethanols, the dicyclopentadienediols, the norbornenediols, the norbornanediols, the cyclooctanediols, the cyclooctenediols, the cyclooctadienediols, the cyclohexanediols, the cyclohexenediols, cyclopentane-1,3-diol; bicyclopentane-1,1'-diol; decahydronaphthalene-1,5-diol; trans,trans-2,6-dimethyl-2,6-octadiene-1,8-diol; 5-methylol-5-ethyl-2-(1,1-dimethyl-2-hydroxyethyl)-1,3-dioxane; 3,9-bis(1,1-dimethyl-2-hydroxyethyl)-2,4,8,10-tetraoxaspiro[5.5]undecane; 3-methyl-2,2-norbornanedimethanol; 5-norbornene-2,3-dimethanol; norbornane-2,3-trans-dimethanol; perhydro-1,4:5,8-dimethanonaphthalene-2,3-trans-dimethanol; perhydro-1,4:5,8:9,10-trimethanoanthracene-2,3-trans-dimethanol; and 5-norbornene-2,3-dimethanol; norbornanolmonomethanols; and norbornenols.

6. The process of claim 4, wherein the aliphatic hydroxyl containing material may additionally be selected from the group consisting of alkoxylated phenolic reactants including ethoxylated catechol, ethoxylated resorcinol, ethoxylated hydroquinone, and ethoxylated bisphenol A; alkoxylation products of the hydrogenated aromatic phenolic reactants included ethoxylated hydrogenated bisphenol A; neopentyl glycol, trimethylol propane, ethylene glycol, propylene glycol, triethylene glycol, higher alkoxylated ethylene glycols, pentaerythritol, 1,4-butanediol; 1,6-hexanediol; and 1,12-dodecandiol.

7. The process of claim 4, wherein the aliphatic or cycloaliphatic hydroxyl containing material comprises one or more cyclohexanedialkanols or cyclohexenedialkanols.

8. The process of claim 7, wherein the aliphatic or cycloaliphatic hydroxyl containing material comprises cis-, trans-1,3- and 1,4-cyclohexanedimethanol; cis-, trans-1,2-cyclohexanedimethanol; cis-, trans-1,3-cyclohexanedimethanol; cis-, trans-1,4-cyclohexanedimethanol; a methyl substituted cyclohexanedimethanol, including 4-methyl-1,2-cyclohexanedimethanol or 4-methyl-1,1-cyclohexanedimethanol; 1,1-cyclohexanedimethanol; a cyclohexenedimethanol including 3-cyclohexene-1,1-dimethanol; 3-cyclohexene-1,1-dimethanol, 6-methyl-; 4,6-dimethyl-3-cyclohexene-1,1-dimethanol; cyclohex-2-ene-1,1-dimethanol; 1,1-cyclohexanediethanol; 1,4-bis(2-hydroxyethoxy)cyclohexane; 1,4-cyclohexanediethanol; 1,4-(2-hydroxyethyloxy)cyclohexane; and 1,4-(2-hydroxyethyloxy)cyclohex-2-ene.

9. The process of claim 1, wherein the epihalohydrin comprises epichlorohydrin, epibromohydrin, epiiodohydrin, methylepichlorohydrin, methylepibromohydrin, methylepiiodohydrin, or any combination thereof; and wherein the ratio of the epihalohydrin to the aliphatic or cycloaliphatic hydroxyl containing material is from about 1:1 to about 25:1 equivalents of epihalohydrin per hydroxyl group in said aliphatic or cycloaliphatic hydroxyl containing material.

10. The process of claim 1, wherein the non-Lewis acid catalyst comprises one of an ammonium, phosphonium, or sulfonium salt.

11. The process of claim 10, wherein the ammonium salt comprises a benzyltriethylammonium salt.

12. The process of claim 1, wherein the basic acting substance comprises at least one of the alkali metal hydroxide, alkaline earth metal hydroxide, carbonate, bicarbonate, or mixtures thereof.

13. The process of claim 1, wherein the basic acting substance comprises at least one of the alkali metal hydroxide, alkaline earth metal hydroxide, carbonate, bicarbonate, or mixtures thereof.

14. The process of claim 13, wherein the basic acting substance comprises sodium or potassium hydroxide.

15. The process of claim 1, wherein the separation process step (II) comprises rotary evaporation, fractional vacuum distillation, short path distillation, packed column distillation, spinning band column distillation, falling film distillation, wiped film distillation, steam distillation, filtration including vacuum filtration, gravity filtration, nanofiltration, microfiltration and ultrafiltration, membrane separations including pervaporation and vapor permeation, centrifugation, water washing or extraction, solvent extraction, supercritical fluid extraction, decantation, column chromatography, electrostatic coalescence, adsorption, or combinations thereof.

16. The process of claim 15, wherein the separation process step (II) comprises a distillation process; and wherein the distillation process comprises a fractional vacuum distillation, a falling film distillation, a wiped film distillation, or combinations thereof.

17. The process of claim 1, wherein the reaction process step (I) is conducted at a temperature of from about 20° C. to about 120° C., at a pressure of from about 20 mm Hg vacuum to about 100 psi, and at a time period of from about 1 hour to about 120 hours.

* * * * *